United States Patent [19]

Faani et al.

[11] 4,079,416
[45] Mar. 14, 1978

[54] ELECTRONIC IMAGE ANALYZING METHOD AND APPARATUS

[75] Inventors: Siamac Faani; Ralph M. Chambers, Jr., both of Ferguson; Jack R. Obst, Florissant; Robert L. Klamm, St. Charles, all of Mo.

[73] Assignee: Barry-Wehmiller Company, St. Louis, Mo.

[21] Appl. No.: 636,440

[22] Filed: Dec. 1, 1975

[51] Int. Cl.² ............................................. H04N 7/18
[52] U.S. Cl. ................................... 358/106; 358/107; 235/92 MT
[58] Field of Search .................. 178/6, 6.8, DIG. 37, 178/DIG. 33; 235/92 MT, 92 DN, 92 CA; 356/168; 250/563; 358/106, 107

[56] References Cited

U.S. PATENT DOCUMENTS

| | | | |
|---|---|---|---|
| 2,798,605 | 7/1957 | Richards | 178/6 |
| 3,740,466 | 6/1973 | Marshall | 178/6.8 |
| 3,751,582 | 8/1973 | Wernikoff | 358/257 |
| 3,777,169 | 12/1973 | Walter | 178/DIG. 37 |
| 3,836,710 | 9/1974 | Takahashi | 178/DIG. 33 |
| 3,932,703 | 1/1976 | Bolsey | 178/6.8 |
| 3,936,800 | 2/1976 | Ejiri | 178/DIG. 33 |
| 3,958,078 | 5/1976 | Fowler | 178/6.8 |
| 3,969,577 | 7/1976 | Lloyd | 358/136 |
| 4,002,823 | 1/1977 | Van Oosterhout | 358/106 |
| 4,006,296 | 2/1977 | Peterson | 358/106 |

*Primary Examiner*—Howard W. Britton
*Attorney, Agent, or Firm*—Gravely, Lieder & Woodruff

[57] ABSTRACT

An electronic image analyzer which is adapted to inspect a given transparent object or a succession of similar objects by producing an illuminated image of the object on a photoelectronic sensor which is then electronically scanned for the purpose of inspecting the image within an electronic look window having the shape of a standard object contour, the shape having been previously stored electronically and capable of being called out through suitable circuits so as to be superimposed on the image. Further, arbitrarily shaped masks may be generated separately or in combination and superimposed on portions of the image within said electronic look window so as to obscure areas which interfere with the inspection process of other areas. Further, the analyzer may be adapted to compare the physical characteristics of a succession of dissimilar objects by superimposing the electronic look window on the images of the objects and rejecting those objects whose shapes or sizes do not conform with the stored standard contour information.

24 Claims, 12 Drawing Figures

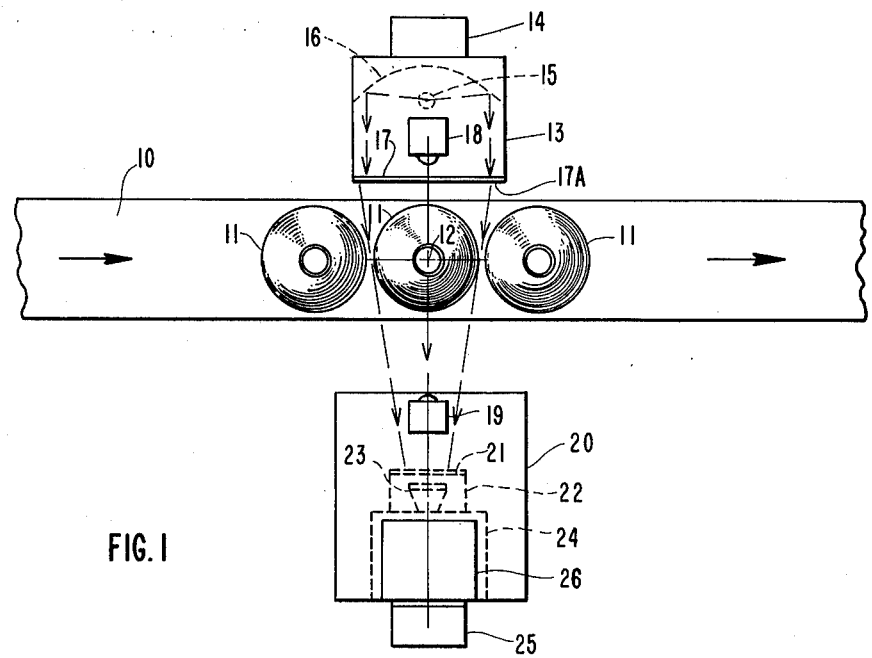
FIG. 1
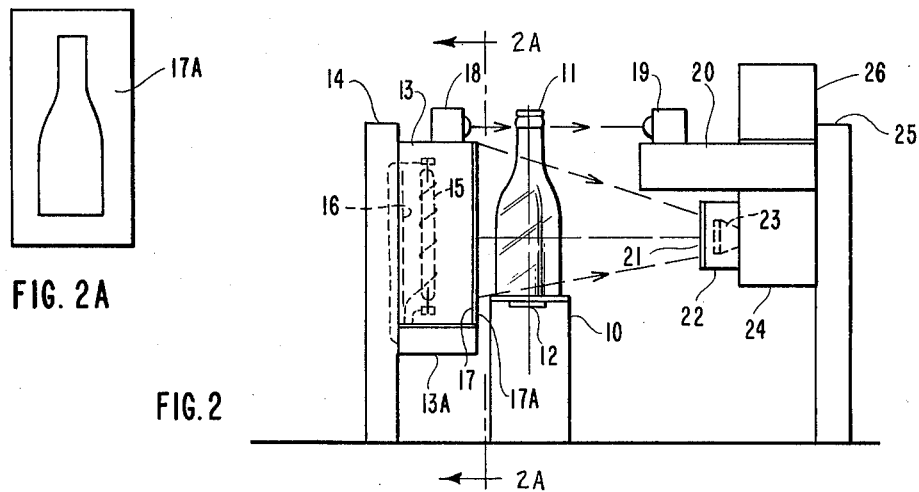
FIG. 2A
FIG. 2
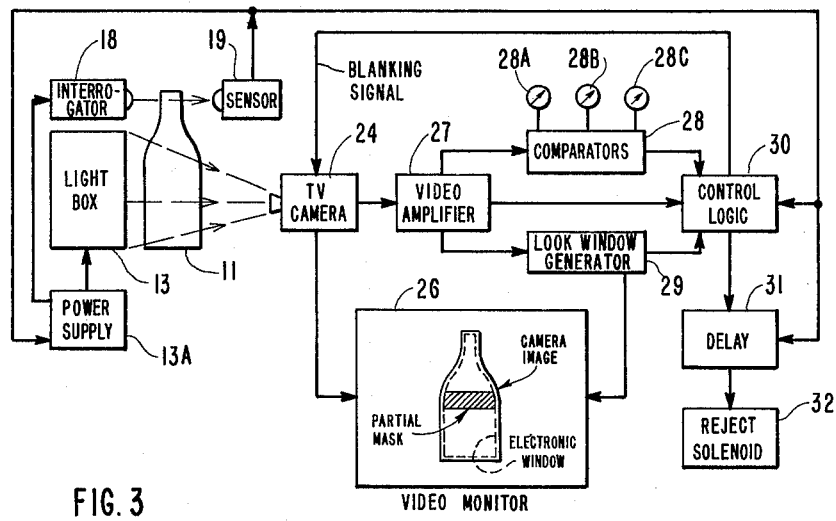
FIG. 3

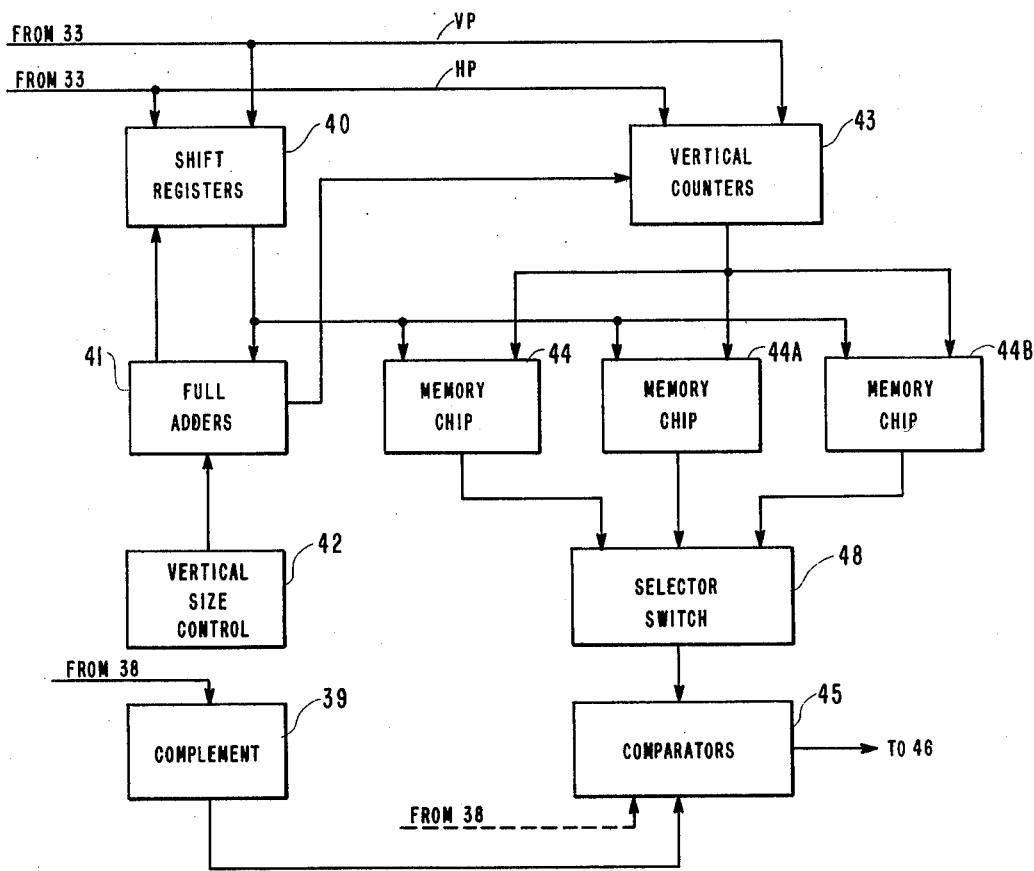
FIG. 8
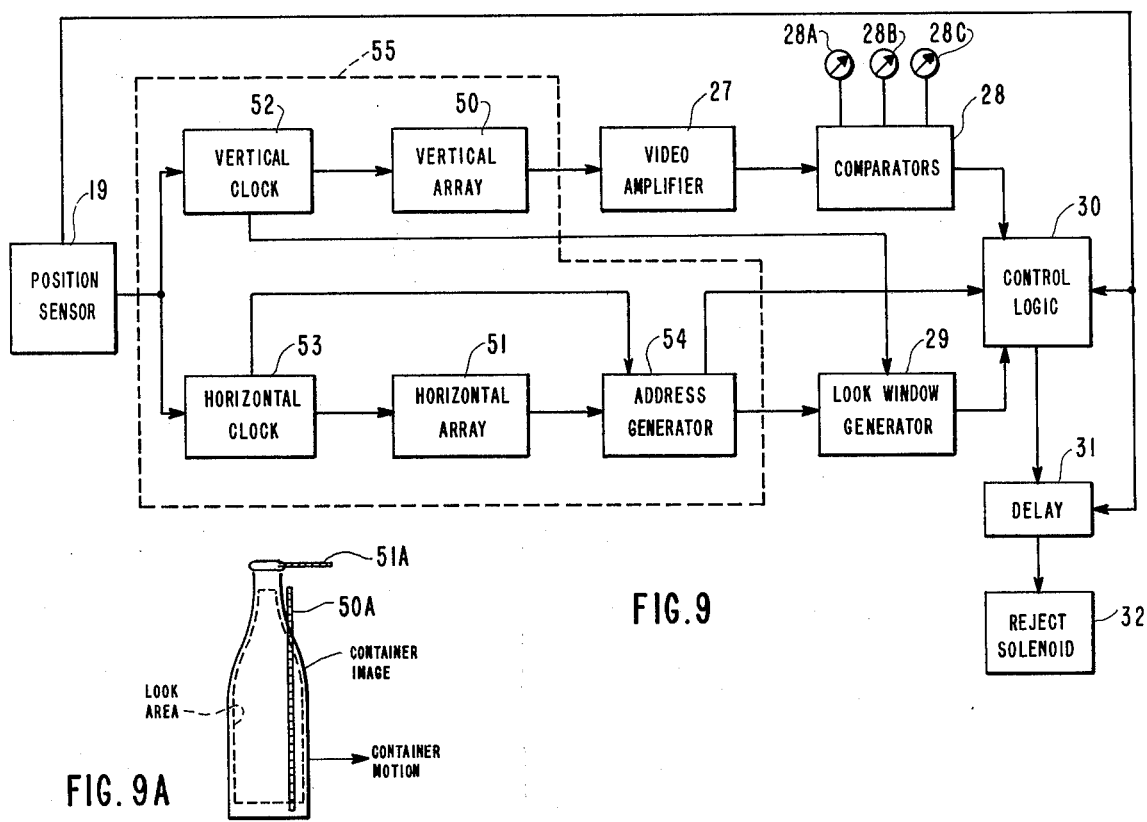
FIG. 9
FIG. 9A

ELECTRONIC IMAGE ANALYZING METHOD AND APPARATUS

SUMMARY OF THE INVENTION

This invention relates to electronic image analyzers, and particularly to electronic apparatus for analyzing the images of transparent objects, such as containers used by the food and beverage industries.

It is particularly important in dealing with food stuffs and beverages designed for human consumption to be sure that the commercial containers are free of foreign material that could cause spoilage or be detrimental to human beings. The ever increasing need for handling vast numbers of containers to meet commercial requirements calls for high speed inspection equipment with the ability to accurately and meticulously scan containers for foreign objects. The speed of travel of containers in inspection systems has gone beyond the ability of apparatus currently available.

Previous electronic inspection devices have been limited by their ability to distinguish shadows generated by the design of the container and the light source from unwanted objects. Such devices can only detect flaws and foreign objects which exhibit markedly greater contrast than the intrinsic shadows. This characteristic severely limits the ability of these devices to detect small or low contrast flaws and foreign objects even though a diffused light source is used to soften the shadows to the greatest possible degree. The electronic look window featured herein makes it possible to inspect the clear portions of the container at a high sensitivity regardless of the nature of spurious shadows which may exist in other areas.

It is, therefore, an important object of the present invention to provide high speed and accurate electronic apparatus for analyzing the images of transparent objects, such as containers, as the objects are moved at high speed through an inspection station, and to incorporate in such apparatus means for inspecting the actual image of the transparent objects within a pre-created and stored electronic look window having the general shape of a normal or preferred contour. It is also an object of this invention to provide apparatus of the foregoing character in which an electronic look window is produced by graphically writing the contour of the object into a memory chip, and to provide an electronic circuit which is capable of calling out the electronic look window as required so that it may be superimposed upon the actual image of a succession of objects for the purpose of detecting significant changes in the light levels caused by flaws or foreign objects, or other matter of a nature that would require the rejection of such objects.

Other objects of the present invention are to provide an electronic analyzer having the ability to illuminate successive containers moving at high speed with short duration pulsing light, to produce true and undistorted images of the individual containers; to provide a single photoelectronic sensing device, such as a TV camera, to scan partial or entire container images; to provide an electronic circuit arrangement capable of calling out and superimposing independently derived and electronically stored contour information onto the image of a single object or images of a succession of objects, and to provide apparatus in which the electronically stored contour information may be created from mechanical data characterizing the physical contour of a standard container so that the mechanical data may be translated into machine language acceptable to computers.

In one embodiment of the invention which employs a TV camera and a short duration pulsing light, it is an object to enhance the inspection capability by making use of the memory inherent in the vidicon camera tube. Since there is no fixed time relation between the light pulses which impress the image on the vidicon tube and the motion of the electronic beam which scans the image and translates it into a video signal, any attempt to read the image immediately after a pulse can result in an inferior video signal generated partly in one field and partly in the next. This difficulty is overcome by the control circuits which do not permit analysis of the image light levels to begin until the electronic beam has returned to its starting point. The method is workable because after each light pulse the vidicon tube will retain a useable image for several fields.

The invention is also directed to electronic image analyzers having the ability to use computer generated mathematical data concerning the contours of transparent containers stored in an electronic storage chip capable of having its information electronically called out when needed for superposition onto the image of an actual container.

A preferred embodiment of the present invention includes apparatus consisting of an inspection station having a light source on one side for illuminating transparent containers, an image sensing device on the opposite side for capturing an image of the illuminated container so that the light levels of the image can be analyzed for flaws that cause significant changes in the light levels, means for producing an electronic look window for superimposing onto the illuminated image, and means to compare the flaws and other matters within the look window against standard container characteristics whereby the detection of the light level changes will trigger a reject mechanism to remove such containers from the flow of a succession of containers through the analysis station.

BRIEF DESCRIPTION OF THE DRAWINGS

The present invention is shown in presently preferred forms by the accompanying drawings, wherein:

FIG. 1 is a schematic plan view of the essential components of the present apparatus;

FIG. 2 is a schematic side view of the different assemblies seen in FIG. 1;

FIG. 2A is a view of a plate in front of the light source formed with an opening shaped to match a container as seen along line 2A—2A in FIG. 2;

FIG. 3 is the electrical block diagram of the system and includes a typical representation of an electronic look window and a partial mask within the image of a container viewed by the camera;

FIG. 8 is a modified electrical block diagram of the memory network in which a plurality of differently programmed memory chips may be incorporated on a selective basis;

FIG. 9 is a modified block diagram showing how two linear solid state scanners can be used for image analysis;

FIG. 9A shows the container image projected onto the linear scanners and the look area on the container as it sweeps past the vertical scanner.

DETAILED DESCRIPTION OF THE APPARATUS

Figure 4:
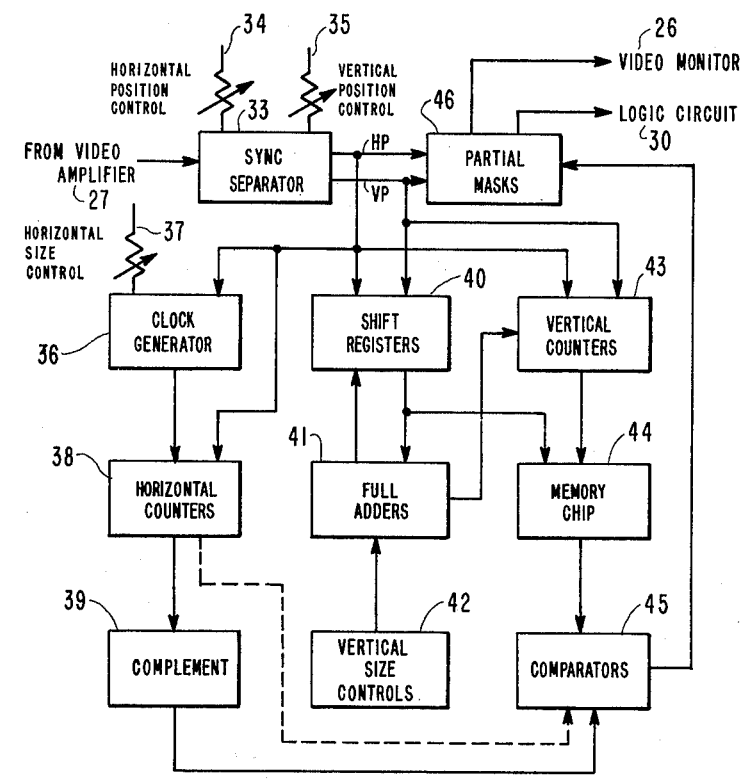
FIG. 4 is an electrical block diagram of the memory network used for producing the electronic look window.

The following description will refer to transparent containers, but it is understood that the objects being analyzed can be other than containers, and the light level analysis can be made of the objects whether they are light transparent or merely produce a silhouette that can be compared to a desired standard.

Referring to FIGS. 1 and 2, conveyor 10 carries containers 11 in succession through the inspection station 12. The container at station 12 receives diffused light rays from the light box 13. The light box 13, supported on column 14 contains a light source 15, a reflector 16, a diffusing window 17, an aperture plate 17a (FIG. 2A), together with necessary supporting mechanisms. The light source 15 is a linear flash tube located at the focus of a parabolic-cylindrical reflector 16. A high voltage power supply 13A (FIG. 2) is connected to the tube 15, to cause the tube to produce a momentary flash of light when the container is sensed by devices 18 and 19 at inspection station 12. The arrival of container at station 12 interrupts a beam of light emanating from device 18 and received by a sensor 19, thereby producing a pulse to activate the light source 15 which illuminates the container. Concurrently the pulse from sensor 19 triggers the inspection circuits within box 20. The arrangement shown in this disclosure is intended to be compatible with high speed conveyors carrying containers in a continuous stream.

Referring back to FIG. 1, the short duration light pulse from tube 15 (less than 0.5 millisecond) illuminates the container at station 12. A television camera 24 is used to receive an image of the container at station 12 through a suitable lens system 23 attached to the camera 24. Since a TV field takes about 16.6 milliseconds for complete scanning of the image, a 2.5 inch diameter container moving at a speed of 800 per minute will move about 0.55 inch in the period required for one scan. Under steady lighting this movement will result in a blurred and distorted image that cannot be processed for inspection. Because of this, a pulsed light source is used to impress a sharp image of the container on the screen that will not be affected by container motion, thus achieving inspection at high speeds. Optical filter assembly 21 supported by frame 22 is used in front of the lens system 23 to compensate for color variations in different containers, as well as to attenuate the ambient light reflections. The camera 24 is located at a suitable distance from the container so that the lens system can project a suitable image of the container onto the photosensitive surface of the sensing element (not shown) within the camera. Provision is made for the camera 24 to move up and down on the column 25 (FIG. 2) so that the optical axis of the camera 24 can be aimed at a desired location on the container 11.

Referring to FIG. 3, a schematic electrical block diagram of the whole system is shown. The video signal representing the image of the container is produced by the camera 24. The signal from the camera is fed to a video amplifier 27 that amplifies and conditions the camera signals for further processing. It should be mentioned that the signals coming out of the camera contain not only the signals associated with the container image but also undesired signals due to elements in the vicinity of the container image, such as the edges of the light box, adjacent containers and edges of conveyors. All these analog signals are fed into network 28 which comprises a combination of comparator circuits designed in a manner to detect light-to-dark, dark-to-light, and absolute changes in light levels within the image area of the camera. Sensitivity controls 28A, 28B and 28C are provided on the network 28 to establish threshold levels for the above mentioned comparators, so that signal levels due to the objects within the image area can be compared with adjustable reference levels set by these sensitivity controls.

The successful inspection of containers requires the automatic inspection machine to distinguish the signals due to the container at station 12 from the undesired signals coming from the edges of containers and other objects in the vicinity of the said container as explained above. In order to achieve this, another output of the amplifier 27 that contains the horizontal and vertical synchronizing pulse trains of the camera is fed to the electronic look window generator 29. This network contains an electronic memory chip together with associated digital circuits that produce an electronic look window (ELW) through which the signals from the comparator network 28 can be analyzed more particularly. This network consists of a suitable arrangement of an electronic memory chip that stores independently derived information describing the physical characteristics (contour, size, etc.) of the container, and other electronic circuits that enable the stored information to be read out or "called out" with the introduction of the synchronizing pulse trains from amplifier 27 into the window generator network 29.

In order to understand the relationship between the camera image and the look window it is possible to view these signals on a video monitor. This is shown in FIG. 3 where a monitor 26 accepts the container signals from the camera 24 together with a suitable portion of the look window in analog form coming from the look window generator 29. This arrangement causes a visual representation of the electronic look window to appear on the monitor in proper relationship to the image of the object. It is an aid for aligning the look window with regards to the image signals coming from the camera 24.

Necessary controls are provided to adjust the size and position of the (ELW) horizontally and vertically so that the window can accurately be superimposed on the container image viewed by the TV camera, as is shown by the monitor 26 which allows the operator to watch the operation of the apparatus. It is through this electronic look window (ELW) that the container image is inspected for flaws and other foreign matters carried by the container. The output of network 29 feeds the control logic 30. A portion of signals from control logic 30 is fed back to the camera 24 for blanking it during the pulsed illumination of the container. Due to the asynchronous relationship between the electron beam scanning the face of the photosensitive element in the camera and the object sensing pulse from the position sensor 19, if the electron beam scanned the image as soon as it was impressed on the camera, a non-uniform image reading would result when the reading process extended to two fields. In order to prevent this, the blanking pulse going from the control logic 30 to the camera 24 is initiated by the object sensing pulse and is made to blank out the electron beam in the camera so that a uniform image is impressed on the camera. The next vertical synchronizing pulse after the object sensing pulse will restore the electron beam to normal, so that the beam may read a complete field starting from the beginning of the field rather than portions of different fields which will otherwise give a non-uniform image reading thus resulting in an unreliable inspection process. Control logic 30 will produce a reject signal only if a flaw is detected within the electronic look window. The reject signal coming from control logic 30 feeds a delay network 31 which under the effect of timing pulses from position sensor 19 will delay the reject until the container with the flaw arrives at a suitable reject station. The delay network 31 comprises electronic circuits arranged as a chain of shift registers to follow the container movement along the conveyor until it arrives at the reject station. The faulty container will then be rejected out of the mainstream by a solenoid mechanism 32 which is energized by the delayed reject pulse from network 31.

FIG. 4 represents the general block diagram of circuits used in the electronic look window generator 29, and their relationship with the electronic memory chip 44. The process of storing the information concerning the contour of the container within the memory chip 44 is as follows: Assuming a standard TV camera system for the photo-electronic device, the 525 lines per TV frame will result in 262.5 lines per field which is utilized in this disclosure for container inspection. The availability of synchronizing pulses together with a suitable number of lines per field enables a system of digital electronics to be successfully applied for the production of an accurate electronic look window (ELW) compatible with the contour of the container. Based on relation (2) $^8 = 256$, a system of eight-bit binary numbers can be used to digitize the contour of the container and store it in a memory chip. A memory chip having storage capacity of 256 memory words with 8 bits of information per word, namely 2048 bits, is sufficient for this purpose. There are different types of memory chips commercially available for this requirement. An Intel Corporation's programmable Read-Only-Memory (ROM) type 1702 is used in apparatus according to this disclosure.

Figure 5:
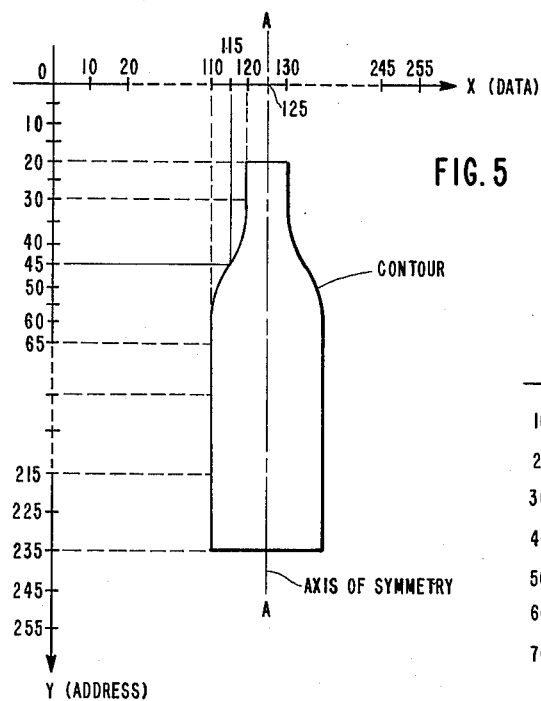
FIG. 5 shows a method of representing the contour of the container in the X-Y plane.

In order to transfer the analog contour information into the memory chip and thus create an electronically simulated contour, the information must be written in suitable machine language. Independent graphical derivation is a good example. To achieve this, a sample container template is selected (FIG. 5) and its outline is plotted on a suitable scale ratio on graph paper Cartesian coordinates, such that the maximum dimension of the contour will occupy a reasonable number of equal gradings on the graph paper containing numbers from zero to 255. This range of zero to 255 gradings on the Y-axis represents 256 TV scan lines as well as 256 memory words necessary for programming the memory chips. A typical arrangement of the contour coordinates is shown in FIG. 5. The numbers on the Y-axis show the actual number of TV scan lines, and the ones on the X-axis are required for defining any point on the contour, and are selected for the purpose of programming the memory chips. For the typical container shown in vertical form in FIG. 5, it is only necessary to define a data X-number for each corresponding address Y-number for the left half of the container symmetrically arranged about the main or longitudinal axis AA of the container contour. Necessary circuits are provided to complement the right half of the contour and thus provide a final electronic contour of the container as a whole.

Returning to FIG. 5, for every address Y-number, the corresponding data X-number must be extracted. It will be noticed that some portions of the contour will not produce a whole X-number for every whole Y-number. For these points on the curve, the closest whole X-numbers will be chosen so that the overall points so chosen on the curve will simulate the contour as accurately as possible. Having established all the necessary X-numbers for corresponding Y-numbers, these data are tabulated in a sequential form starting from address-number zero to address-number 255. As mentioned above, in order to feed this information into the memory chip 44, the data must be translated into a machine language. All the decimal numbers are, therefore, translated into octal and binary forms. Different programming machines can be used to "write" this information into the memory chip 44. There are manual programmers which can directly accept the digital information. Or the X-Y information for each point can be punched into an IBM card (not shown) that carries information for one point. There must be 256 cards prepared in this manner for all X-Y information. It should be noted that for this arrangement, the address Y-number is typically in the octal form, and the data X-number is punched in 8-bit binary form. Arranging the punched cards in sequential form, they are fed into a suitable automatic programmer with the memory chip 44 in position and thereby "write" the final program into the chip. The memory chip programmed in this way will store the simulated contour information which can be called out to be superimposed on the image information of the container, as seen in the video monitor 26 in FIG. 3.

Figure 6:
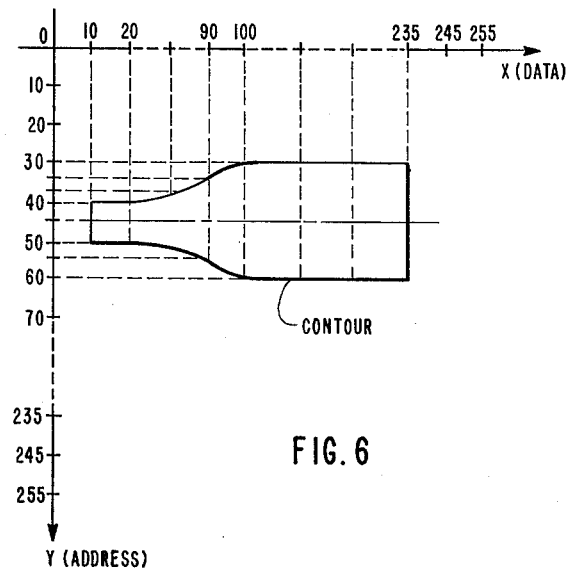
FIG. 6 shows another method of representing the contour of the container in mathematical form.

On the other hand, FIG. 6 shows a container contour drawn in a horizontal form. For this configuration there is no axis of symmetry along the Y-axis and therefore, the whole contour may be translated into digital form and thus no complementing circuits are required.

Figure 7:
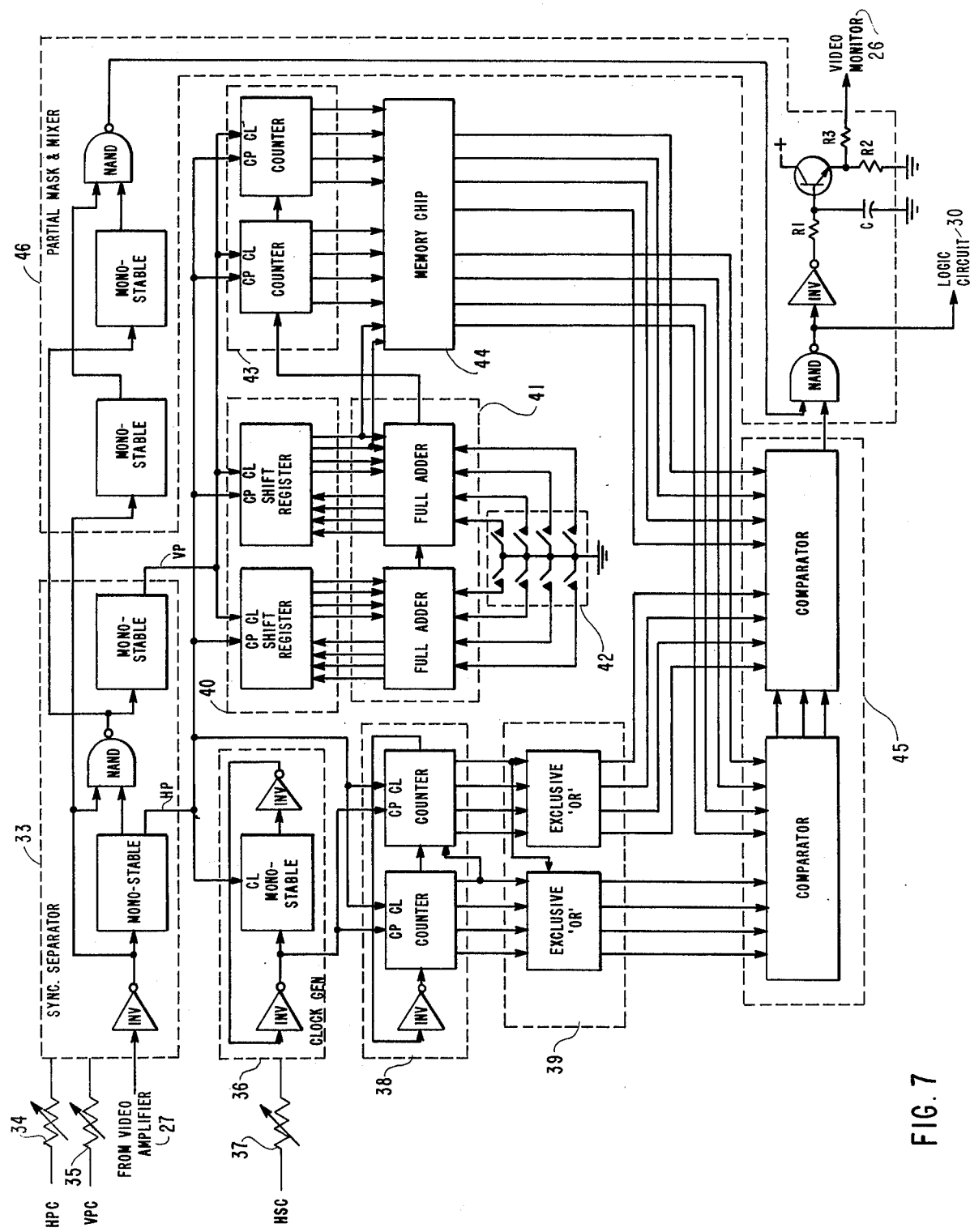
FIG. 7 is a block diagram of a typical network utilized for recovering the stored information on the electronic look window.

Referring to FIG. 4 and FIG. 7, there are shown the block diagrams of the typical circuits constituting the electronic look window generator 29 in FIG. 3. The combined horizontal and vertical sync pulses from the video amplifier 27 feed the sync separator circuit 33. This circuit separates the horizontal sync pulses from vertical sync pulses and includes delay circuits for establishing the start of the electronic look window in horizontal and vertical coordinates that can be adjusted by means of potentiometer controls 34 and 35 respectively. The circuit 33 (FIG. 7) consists of monostable multivibrators together with associated timing components and suitable inverters and gates. The horizontal position (HP) pulses feed a clock generator circuit 36, that consists of a monostable multivibrator circuit with timing components and inverters arranged in free-running mode to generate suitable clock pulse trains for the horizontal coordinate counters. Potentiometer 37 adjusts the frequency of the clock pulses between approximately 2 MHZ and 10 MHZ and enables adjustment of the horizontal size of the look window as desired. The HP pulses from circuit 33 are used to inhibit the generation of clock pulses during the interval between the start of each horizontal sync pulse and the start of the electronic look window. The clock pulses thus produced feed the horizontal counter circuit 38. This circuit is composed of two high speed synchronous 4-bit counters cascaded to form an overall 8-bit counter to generate the horizontal coordinate count from zero to 255. The outputs from circuit 38 are fed to network 39 which consists of "exclusive-or" gate circuits to generate the complements of the input pulses so that the right hand portion of the electronic look window symmetrical to the left hand portion is also produced. The outputs from network 39 contain the digitized horizontal information to be used for comparison with information stored in memory chip 44. In order to condition the vertical counting, horizontal position (HP) and vertical position (VP) pulses from circuit 33 are fed to an 8-bit shift register network 40 that consists of two 4-bit parallel-access register chips. This circuit stores the necessary vertical coordinate count, and together with the 8-bit binary full adder circuit 41 and control switches 42, determines the vertical size of the electronic look window. The resultant carry output from the adder network 41 feeds the 8-bit counter 43 whose outputs together with portions of outputs from shift register 40 address the memory chip 44 that contains the horizontal window coordinates corresponding to their vertical coordinates; the chip 44 having been programmed as explained before. The outputs from the memory chip 44 and complementing circuit 39 enter the 8-bit comparator network 45 which is composed of two 4-bit magnitude comparators. This network compares the current horizontal coordinate count produced by circuit 39 with the data stored in memory chip 44 corresponding to the current vertical count. The output of the comparator circuit 45 is the electronic look window (ELW) representing the desired characteristics of the container.

If the contour layout shown in FIG. 6 is used for programming the memory chip 44, there will be no image symmetry in the Y-axis direction, and thus the complementary network 39 will not be needed. The outputs of the counter 38 would then be fed directly to the comparator 45 to be processed along with the information coming from the memory chip 44. The digitized contour (ELW) from network 45 is then fed (FIG. 7) to partial mask circuit 46. This network consists of suitable circuits for producing partial masks of rectangular form or stored masks of different shapes processed as explained for memory chip 44, that can be adjusted in size and position to be superimposed on the main electronic look window shown in the video monitor 26 of FIG. 3. The partial masks may be used for blocking portions within the electronic look window (ELW). This is of special interest in situations where the containers have certain undesirable abnormalities such as labels and/or letterings which would make the overall container inspection impossible. Under these conditions partial masks can selectively be used within the (ELW) to exclude label areas and inspect other portions of the container for foreign objects. The combined electronic look window (ELW) and the partial masks in circuit 46 are then conditioned and fed to the control logic 30. The video monitor 26 in FIG. 3 shows the relationship between the (full line) actual container image viewed by the camera and the (broken line) electronic look window (ELW) that is produced by programming the desired characteristics of the container and storing it in a suitable memory chip, and a partial mask within the window.

FIG. 8 shows a modified electronic block diagram for the purpose of indicating the versatility of the present invention. The various components in this circuit have been described previously and are designated by similar reference numbers. In this circuit a plurality of memory chips 44, 44a and 44b are selectively placed in the operative circuit by means of a selector switch 48, thereby adapting the circuit for the examination of different shaped containers. For example the memory chip 44A could be programmed for a pint size container, and memory chip 44B could be programmed for a quart container, assuming that chip 44 is programmed for a 12 oz. container. In view of this versatility, it is to be understood that the present invention may be utilized to examine a variety of different objects, and by providing a plurality of memory chips together with a selector switch, the examination of objects may be carried out with a minimum of set up time and with great convenience to the operator.

The above mentioned circuits called out in the block diagram may be commercially available high speed integrated circuits. In this disclosure, Transistor-Transistor-Logic (TTL) chips in the standard 74 series are used. A typical wiring arrangement is shown in FIG. 7.

In place of a standard television camera using a vidicon tube as its photo-electronic scanning device a system of linear photodiode arrays can be utilized. There are different types of solid state photodiode arrays available commercially for the purpose of electronic image sensing and analysis. A typical scanner made by Reticon Corporation can be chosen to have a row of 256 photodiode elements together with integrated circuitry containing the necessary switching and shift register circuits all enclosed in one package. This type of scanner would be comparable to 262.5 lines used in a standard TV camera. Two such linear arrays may be chosen for controlled scanning of the container image, and FIG. 9 shows a typical block diagram of the two photodiode arrays 50 and 51 and the necessary circuits for processing container images produced by illuminating the objects at the inspection station. It should be mentioned that for this application, the preferred light source is of steady nature (not shown) rather than the pulsing type used for TV camera application. FIG. 9A shows the positional relationship between the container image (full line) and photodiode array 50A in array circuit 50 which is physically arranged in a manner so that an optical system of the type mentioned above will allow the container image to be focused on the diodes 50A. Provision can be made to align the array along the longitudinal axis of the container. As the container is moved across the station, its image will sweep past the photodiode array 50A in the linear scanner 50. A second linear scanner 51 is located to accept collimated rays from a well defined source on its diode array 51A shown in FIG. 9A. This array 51A is used for sensing the instantaneous container position as it moves across the inspection station. Under normal conditions this array 51A is illuminated with the collimated rays. As the container neck cuts the light rays, different numbers of photodiodes in array 51A will be blocked such that signals coming from the blocked diodes can be used for commanding the vertical array 50A to scan the length of the container at that container location. As the container moves further through the station, new photodiodes are blocked in array 51A, thus giving new command signals to array 50A to scan the length of the container at new locations, and this progressive response continues over the width of the container.

Referring to FIG. 9, devices 52, 50, 53, 51 and 54 shown within the dotted box 55 replace the TV camera 24 (FIG. 3) to achieve the inspection of the containers. Position sensor 19 senses the arrival of container at the inspection station. Pulses from sensor 19 control the clock pulse generator 52 for vertical scanning and clock pulse generator 53 for horizontal scanning. Output of circuit 52 feeds the vertical array 50 and enables the array to scan along the length of the container. Output of array 50 is a serial train of analog signals representing the outputs of the photodiodes. These signals are fed to the video amplifier 27 (previously seen in FIG. 3) that amplifies signals for further processing as explained before. Clock generator 53 feeds the horizontal array 51. As the container moves across the station, sufficient numbers of photodiodes in array 51A will be blocked and by suitable choice of the rate of clock pulse from generator 53, a pulse train will emerge from array 51 which is an indication of instaneous position of the container at the inspection station. The output of array 51 feeds the address generator 54. This address circuit also accepts the clock pulse train from 53 and translates the photodiode outputs from 51 into digital pulse trains that can be used to address the electronic look window generator 29 (previously seen in FIG. 3). The (ELW) circuit 29 also accepts the clock pulses from circuit 52 that controls the scanning of vertical array 50. The look window generator 29 will produce a pulse train that effectively establishes the start out and finish of scanning length along the array 50A (FIG. 9A), and as the container sweeps through the station, a look area on the container will thus be produced. This look area is shown as dotted within the full line container image in FIG. 9A. The process of storing the information on the container contour in a memory chip and recovering it through the electronic look window generator 29 and the operation of the rest of the block diagram is as has been explained above for in FIGS. 3, 4 and 7.

In place of a standard television camera using a vidicon tube as its photo-electronic scanning device, or the linear photodiode array of FIGS. 9 and 9A, a system of solid-state sensors arranged as an area array can be used. There are different types of these arrays available each utilizing different construction technology. However, the type which can readily be adapted to perform the functions required in this apparatus is made by Reticon Corporation. In this type of sensor, each sensor consists of a number of photodiodes arranged in a general format such as a (n × n) or (n × m) diode matrix together with necessary solid-state switching and shift register networks all in a single integrated circuit package. An area array having (256 × 256) photodiodes will therefore constitute a suitable scanner comparable to a standard vidicon tube.

Figure 10:
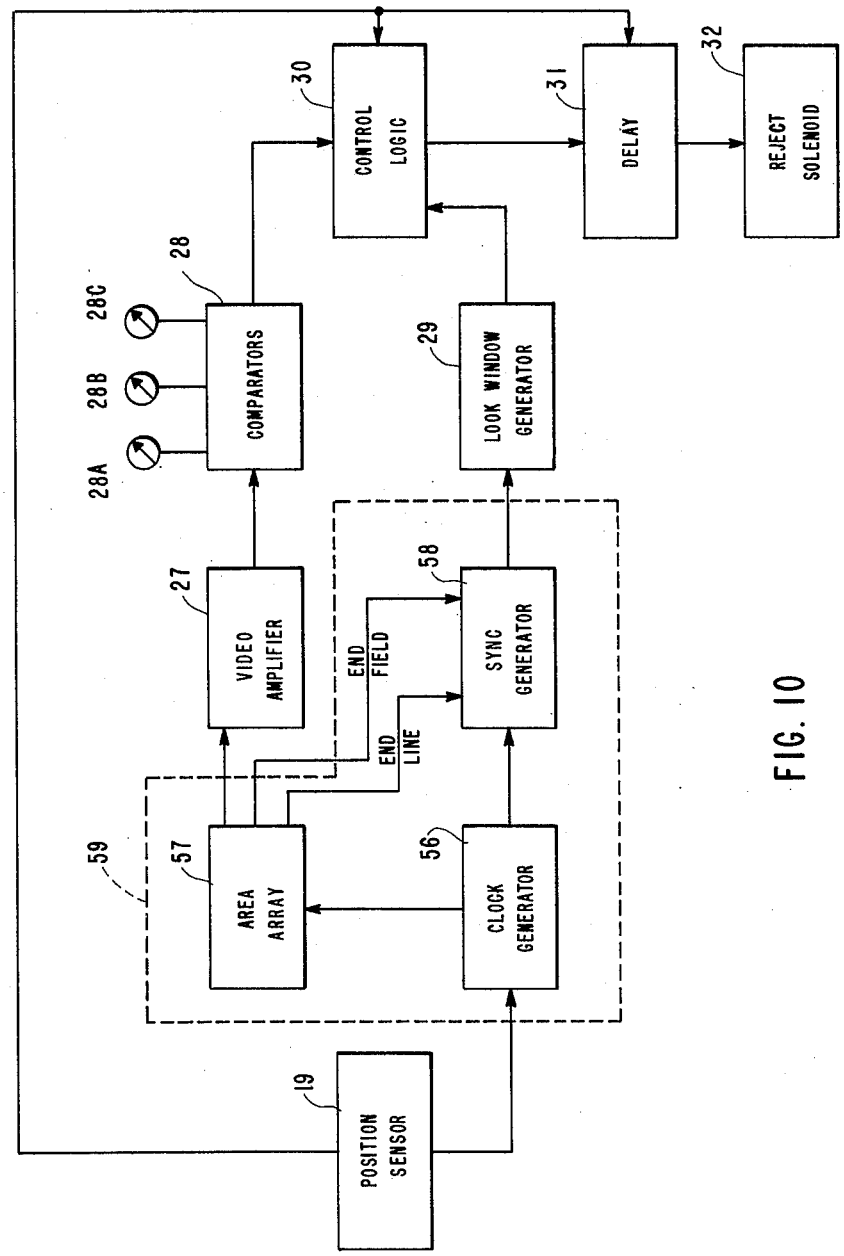
FIG. 10 shows a typical block diagram incorporating a solid state area array for image sensing and analysis.

FIG. 10 shows a typical block diagram of an area array together with networks for processing the container image projected onto the array through a suitable optical system such as that explained for TV scanning. The preferred light source, however, will be a steady light rather than the pulsing type, although the systems can also be made to work with pulsing light source since the array will retain the image signals for a considerable time until scanned for processing.

Returning to FIG. 10, devices 56, 57 and 58 shown in dotted box 59 constitute a solid-state camera that can replace the standard vidicon camera 24 (FIG. 3) to process the container images in the manner explained thereof. Pulses from position sensor 19 feed the clock pulse generator 56 that controls the scan rate of area array 57. The clock rate can be adjusted through control means (not shown) for any desired scanning mode of the array 57. Under the effect of illumination by the light source and the clock pulses from 56, the output of array 57 will be a serial train of analog signals representing the electronic response of photodiodes. This output is fed to video amplifier 27 whose function has already been explained. The array 57 will also produce two extra pulse trains showing the end of each scanned line and that of the scanned field. These pulse trains feed the synchronizing pulse generator 58 that also accepts clock pulses from generator 56. Circuit 58 will produce a pulse train that contains the horizontal and vertical sync pulses, and feed the look window generator 29 to recover the stored container contour information. The functions of the rest of the circuits in FIG. 10 is explained in the circuits for using a standard TV camera system, and like reference numbers have been applied to those circuits.

When a standard TV camera is used for inspection, the light source is pulsed to impress a sharp image on the photosensitive area of the camera. Successful inspection makes this imperative. This is done to freeze the image of the container and thus render the container motion unobjectionable. Momentary illumination is also possible with steady light and either a fast acting optical or an electromechanical shutter to achieve the same image impression on the camera. However, the speed of operation of these shutters will not match that of the flash tube arrangement activated by an electronic pulse.

Successful operation of the TV camera for container inspection requires that the back lighting be directed towards the container in a manner to override the effects of the stray ambient light. This is generally achieved by selecting a light source of sufficient intensity. However, when this light is directed towards the container, the TV camera will see two distinct portions of light coming from the light box 13. A useful portion transmits through the container and highlights the surfaces of the container for the purpose of seeing any flaws against the background of the container. The second portion is the light which does not transmit through the container but emanating from the light box arrives at the lens system 23 in two parts. One part will arrive at the camera directly from the light box. The other part will arrive at the lens system 23 after multiple reflections and refractions through the container. These two unwanted light parts having sufficient intensities will readily be accepted by the photo-sensitive element of the TV camera as the "back" lighting if not eliminated, and will "overwhelm" the vidicon tube resulting in deterioration of relative photosensitivity of the vidicon for the useful light transmitting through the container. In order to eliminate these undesirable effects, an aperture is used on the light box 13 with an opening contoured to the general shape of the container under inspection so that the light emanating from the opening will just envelop the whole body of the container. Such an aperture is formed in the plate 17A (FIG. 2A).

When a solid-state camera is used for image processing, there will be no need for shutters or pulsed light source. A steady light source is sufficient, and the controlled image processing can be achieved by suitable electronics to render the container motion at the inspection station unobjectable. Such a system is seen in FIGS. 9 and 9A where the system is arranged to employ a linear array of solid state photo diodes aligned with the vertical axis of the object being inspected together with another linear array positioned at right angles to the first and disposed to provide the necessary timing pulse as the object moves through the inspection zone.

The foregoing description has set forth the arrangement of several suitable circuits for producing an electronic look window (ELW) for inspection of transparent containers. For inspection of the bottoms of containers and/or the mouths of containers for flaws, the stored information in the memory chip would have a circular plot for the bottoms and an annular plot for the mouths of containers. Various modifications of the foregoing arrangements can be applied to program and store a variety of contours and profiles of objects where it is necessary to inspect the existing ones against a sample of acceptable reference contour for static and/or dynamic conditions. In every case, the sample contour can be programmed into suitable memory chips and can be read out electronically for the purpose of comparison with the actual images produced by a suitable scanner, and a decision can be made on the acceptability of the objects.

What is claimed is:

1. A method of electronically analyzing the image of an illuminated object for significant changes in the light level of a predetermined amount which comprises the steps of: storing in a digital electronic network an electronic look window having the contour information of a standard object derived independently of the object to be analyzed; moving the object to be analyzed in front of a source of illumination; projecting the illuminated object image onto image sensing means to produce signals indicative of the light levels of the sensed image of the illuminated object; feeding the sensed image signals of the illuminated object into a signal processing networks; feeding synchronizing information from the image sensing means into the network containing the electronic look window; electronically relating the two networks to superimpose the electronic look window contour of a standard object on the signals derived from the sensed image signals; and evaluating to a reference level only the signals which appear within the electronic look window and are produced by the light levels of the sensed image.

2. The method set forth in claim 1 wherein the signal processing network identifies light-to-dark, dark-to-light and absolute light level changes of the sensed image, and includes controlling the sensitivity of the network to establish threshold levels for comparison with the sensed image signal levels.

3. The method set forth in claim 1 wherein the digital electronic network contains the independently derived information on the representation of the contour of the standard object and calls out the stored information upon being electronically related to the scanning characteristics of the image sensing means.

4. The method set forth in claim 1 wherein the feeding of the synchronizing information into the digital electronic network includes adjusting the rectilinear coordinates of the established electronic look window to accurately superimpose the electronic look window onto the sensed image.

5. The method set forth in claim 1 and including combining the electronic look window generator network with other circuits for producing partial masking of arbitrarily shaped predetermined portions of the illuminated object image, whereby arbitrary areas of the sensed image signals of the objects which occur within the digital representation of the standard object are masked.

6. The method set forth in claim 1 in which the electronic look window network includes a plurality of memory circuits selectively useful for analyzing objects having different characteristics each independently derived from known sample objects.

7. The method set forth in claim 1 in which the image sensing means produces signals indicative of the illuminated image along one linear dimension of the object and signals indicative of the position of the object along a second linear dimension; electronic means to store information independently derived from said standard object; and other electronic means which varies the inspection length along said one linear dimension according to the shape and position of the object.

8. A method of electronically analyzing physical characteristics of a succession of objects with the predetermined physical characteristics of a known sample object which method comprises the steps of: illuminating the succession of objects serially to produce an illuminated image of each thereof; aligning an image sensing means with the opposite side of the serially illuminated objects to produce signals indicative of the physical characteristics of the sensed image of the objects; feeding the signals of the illuminated images into a signal processing network; feeding synchronized information into a digital electronic network containing stored physical characteristics of the known sample object independently derived to establish a look window; and utilizing the networks to electronically superimpose the look window physical characteristics on the signals from the sensed illuminated images of the successive objects to effect the analysis of the physical characteristics of successive objects within the electronic look window.

9. The method set forth in claim 8 in which the electronic look window generator network includes a plurality of memory circuits selectively useful for analyzing different physical characteristics each independently derived from known samples of objects.

10. The method set forth in claim 8 in which the electronic look window generator network includes a plurality of memory circuits selectively useful for analyzing physical characteristics of different objects.

11. A method of electronically analyzing the images of a succession of like, light-transparent objects moved through an inspection station within the contour of a sample object which comprises: electrically storing the contour of the sample object by deriving it independently of the objects to be analyzed; feeding the actual image of each transparent object into a processing network to develop signals indicative of the light level of the image of the objects moved through the inspection station; and superimposing the stored contour of the sample object on the signals in the processing network to effect the analysis.

12. A method of electronically analyzing images of a succession of transparent objects for objectionable matter which comprises, storing a configuration of a sample object graphically derived independently of the transparent objects images, moving the objects through an inspection station, illuminating each transparent object at the inspection station to develop an image thereof, projecting each image of the transparent objects onto a light sensitive scanner means, inspecting the image of each object within the stored graphically derived configuration of the sample object by aligning the stored graphically derived configuration of the sample object with the projected image, and identifying an object upon detecting any objectionable matter in the projected image which falls within the electronically stored characteristics of a sample object superimposed onto the projected image.

13. A method of electronic comparison of the images of a succession of objects with a simulated electronic contour of a standard object which consists in the steps of, storing an independently derived contour configuration of said standard object to be used as the simulated electronic contour, electronically registering each image of the succession of objects with the stored independently derived contour configuration of the standard object to effect a comparison thereof, and identifying any object whose electronically registered image deviates from said stored independently derived contour configuration of the standard object by a predetermined amount, the said deviation occuring within the stored contour of the standard object.

14. A method of electronically analyzing the illuminated image of a light transparent object having a known contour for significant changes in the light level of a predetermined amount which comprises the steps of: electronically memorizing an independently graphically derived digital representation of the contour of the transparent object to be analyzed and containing that contour in an electronic look window generator network; illuminating an actual transparent object from one side; aligning optical means with the opposite side of the illuminated actual object to project the illuminated image onto image sensing means to develop an image of the contour of the illuminated actual object; feeding the thus developed illuminated image signals of the object from said image sensing means into an image signal processing network; and electronically calling out and registering the independently graphically derived digital representation of a contour image memorized by the electronic look window generator network with the sensed image to analyze the portions of the image which coincide with the independently graphically derived digital representation of the transparent object.

15. Electronic image analyzing apparatus comprising: a source of illumination; means moving objects one at a time past said illumination source; optical means to produce an illuminated image thereof; light sensitive means positioned to receive the illuminated image of each object; illuminated image signal processing circuit network connected to said light sensitive means; look window generator means which contains a contour of a standard object independent of the received image from said light sensitive means and having an electronic network connected to said processing circuit network; and means in said signal processing circuit network to superimpose the look window from said generator means on the image signals of each of the illuminated objects for analyzing the image signals for significant changes in the level of illumination within the said look window.

16. The apparatus set forth in claim 15 wherein said look window generator means having an electronic network includes means storing information representative of predetermined characteristics of the objects to be analyzed, and means to call out the stored information.

17. The apparatus set forth in claim 15 wherein said look window generator means having an electronic network includes means storing information representative of predetermined portions of the standard object, and means to call out the stored information.

18. The apparatus set forth in claim 15 wherein said look window generator means having an electronic network includes a plurality of means, each storing different representative characteristics of different objects to be analyzed, and means selectively operable to call out the stored information from said plurality of storing means.

19. Electronic image analyzing apparatus comprising: a source of illumination; means moving objects one at a time past said illumination source; optical means to produce an illuminated image thereof; light sensitive means positioned to receive the illuminated image of each object; said light sensitive means including a pair of linear photoelectronic sensing arrays arranged with one array substantially parallel to one characteristic dimension of the object and the other array arranged substantially normal to said one array; illuminated image processing circuit network connected to said light sensitive means; look window generator means storing an independently derived contour of a standard object and having an electronic network connected to said processing circuit network; and means in said signal processing circuit network to superimpose the look window from said generator means on the image signals of each of the illuminated objects for analyzing the image signals for significant changes in the level of illumination within the said look window.

20. The apparatus set forth in claim 19 wherein said light sensitive means is a matrix of photoelectronic sensing elements.

21. Apparatus to analyze the image of an illuminated object for changes in the light levels different from a sample object used as a standard, said apparatus comprising: means to support an actual object in a position for analysis; means to illuminate the actual object; means to create an illuminated image thereof; means to sense the illuminated image of the actual object and produce signals indicative of the light levels of the illuminated image; electronic network means connected to said sensing means to process the sensed illuminated image signals; digital electronic network means operable to store a look window that is the independently derived digital representation of predetermined portions of the contour of the sample object; and means electronically relating said look window electronic network and said illuminated image electronic network to superimpose said look window representation of the predetermined portions of the contour of the sample object on the sensed illuminated image signals of the object to effect the analysis for changes in the light levels within said look window.

22. Apparatus for electronically analyzing the image of an illuminated object against a known physical configuration of a sample object for significant changes in the light levels of a predetermined amount, said apparatus comprising: a light source to illuminate the object from one side; optical means and image sensing means directed at the illuminated object from the opposite side, said sensing means producing signals representative of the light levels of the image of the illuminated object; circuit means for identifying the changes in the light levels of the illuminated image; and an electronic look window generator network connected to said circuit means, said generator network having a memory network with digital information graphically derived from the sample object representative of the characteristics of the object to be analyzed stored therein, circuit means activating said memory network to call out and superimpose the digital information of the sample object stored in said memory network upon the sensed image signals of the object to complete the analysis of the object; other circuit means for producing graphically derived partial masks of different shapes; and means selectively combining said partial masks with said graphically derived digital information from the sample object representative of the characteristics of the object to be analyzed to selectively block out areas where analysis is not desired.

23. Apparatus for electronically analyzing the image of an illuminated object against a known physical configuration of a sample object for significant changes in the light levels of a predetermined amount, said apparatus comprising: a light source to illuminate the object from one side; optical means and image sensing means directed at the illuminated object from the opposite side, said sensing means producing signals representative of the light levels of the image of the illuminated object; circuit means for identifying the changes in the light levels of the illuminated image; and an electronic look window generator network connected to said circuit means, said generator network having a memory network with digital information graphically derived from the sample object representative of the characteristics of the object to be analyzed stored therein, said memory network including a plurality of separate memory circuits each with graphically derived digital representations of an object stored therein, and circuit means activating said memory network to call out any one of said separate memory circuits for superimposing its stored sample physical configuration on the sensed illuminated image signals of the object to be analyzed.

24. Apparatus for electronically analyzing the image of an illuminated object against a known physical configuration of a sample object for significant changes in the light levels of a predetermined amount, said apparatus comprising: a light source to illuminate the object from one side; optical means and image sensing means directed at the illuminated object from the opposite side, said sensing means producing signals representative of the light levels of the image of the illuminated object and including first means producing signals indicative of a first linear dimension of the illuminated image, and second means producing signals indicative of a second linear dimension of the illuminated image normal to said first linear dimension and representative of the position of the image during the analysis; circuit means for identifying the changes in the light levels of the illuminated image; and an electronic look window generator network connected to said circuit means, said generator network having a memory network with digital information graphically derived from the sample object representative of the characteristics of the object to be analyzed stored therein, and circuit means activating said memory network to call out and superimpose the digital information of the sample object stored in said memory network upon the sensed image signals of the object to complete the analysis of the object.

* * * * *

UNITED STATES PATENT AND TRADEMARK OFFICE
CERTIFICATE OF CORRECTION

PATENT NO. : 4,079,416
DATED : March 14, 1978
INVENTOR(S) : Siamac Faani, et al

It is certified that error appears in the above-identified patent and that said Letters Patent are hereby corrected as shown below:

Column 1, line 22, after "there" and before "to" delete the word "ability" and substitute "inability". (This error will be found on page 3 of the original specification).

Column 5, line 56, after "paper" insert the word "with". (This error will be found on page 13, line 14 in the original specification).

Column 10, line 2, change "thereof" and insert the word "before". (This error will be found on page 23 of the original specification).

Signed and Sealed this

Twenty-second Day of August 1978

[SEAL]

Attest:

RUTH C. MASON
Attesting Officer

DONALD W. BANNER
Commissioner of Patents and Trademarks